(12) United States Patent
Ahluwalia et al.

(10) Patent No.: US 8,735,144 B2
(45) Date of Patent: May 27, 2014

(54) BIOREACTOR CHAMBER

(75) Inventors: Arti Ahluwalia, Massa (IT); Daniele Mazzei, Pisa (IT); Bruna Vinci, Serra San Bruno (IT)

(73) Assignee: Kirstall Limited, Sheffield (GB)

( * ) Notice: Subject to any disclaimer, the term of this patent is extended or adjusted under 35 U.S.C. 154(b) by 451 days.

(21) Appl. No.: 13/057,068

(22) PCT Filed: Jul. 31, 2009

(86) PCT No.: PCT/GB2009/050964
§ 371 (c)(1),
(2), (4) Date: Feb. 1, 2011

(87) PCT Pub. No.: WO2010/013068
PCT Pub. Date: Feb. 4, 2010

(65) Prior Publication Data
US 2011/0136218 A1   Jun. 9, 2011

(30) Foreign Application Priority Data

| Aug. 1, 2008 | (GB) | 0814033.7 |
| Aug. 1, 2008 | (GB) | 0814034.5 |
| May 15, 2009 | (GB) | 0908400.5 |
| May 15, 2009 | (GB) | 0908404.7 |

(51) Int. Cl.
*C12M 1/12* (2006.01)
*C12M 1/00* (2006.01)
*C12M 1/04* (2006.01)

(52) U.S. Cl.
CPC .............. *C12M 29/04* (2013.01); *C12M 23/34* (2013.01); *C12M 23/24* (2013.01)
USPC .................. 435/297.1; 435/293.1

(58) Field of Classification Search
CPC ...... C12M 21/02; C12M 31/10; C12M 31/02; C12M 31/08; C12M 23/06; C12M 41/00; C12M 29/04; C12M 23/34; C12M 29/10; C12N 1/12; C02F 3/32; A01G 33/00
USPC .................. 435/292.1, 293.1, 297.1
See application file for complete search history.

(56) References Cited

U.S. PATENT DOCUMENTS

| 2004/0109793 A1 | 6/2004 | McNeely |
| 2005/0084954 A1* | 4/2005 | Bader ...................... 435/295.1 |
| 2005/0186121 A1* | 8/2005 | West ........................... 422/103 |
| 2006/0003436 A1* | 1/2006 | DiMilla et al. ............ 435/284.1 |

FOREIGN PATENT DOCUMENTS

| WO | WO 97/44132 A1 | 11/1997 |
| WO | WO 02/072264 A1 | 9/2002 |
| WO | WO 2005/123258 A1 | 12/2005 |

OTHER PUBLICATIONS

International Search Report for PCT/GB2009/050964.

* cited by examiner

*Primary Examiner* — Michael Hobbs
(74) *Attorney, Agent, or Firm* — Myers Bigel Sibley & Sajovec, P.A.

(57) ABSTRACT

Embodiments of the invention provide a bioreactor chamber assembly comprising: a bioreactor chamber comprising first and second portions arranged to be coupled to one another thereby to provide a liquid-tight seal therebetween; a pair of clamp members; and a pair of resilient loop elements, wherein the clamp members are arranged to sandwich the chamber between the clamp members and the loop elements are arranged to apply a force between the clamp members to urge the first and second portions together.

20 Claims, 14 Drawing Sheets ns a 35 U.S.C. §371 national phase
BIOREACTOR CHAMBER

RELATED APPLICATIONS

The present application is a 35 U.S.C. §371 national phase application of PCT International Application No. PCT/GB2009/050964 having an international filing date of Jul. 31, 2009, claiming priority to Great Britain Patent Application No. 0814033.7, filed Aug. 1, 2008; Great Britain Patent Application No. 0814034.5, filed Aug. 1, 2008; Great Britain Patent Application No. 0908404.7, filed May 15, 2009; and Great Britain Patent Application No. 0908400.5, filed May 15, 2009. The disclosures of each application are incorporated herein by reference in their entireties. The above PCT International Application was published in the English language as International Publication No. WO 2010/013068 A2.

FIELD OF THE INVENTION

The present invention relates to chambers for bioreactors.

BACKGROUND

It is known to provide a bioreactor having a culture chamber and means for passing a flow of culture medium through the chamber in order to enable a wide range of studies of biological materials. By way of example, the biological material under investigation may be a monolayer cell culture, scaffold culture or tissue slice. WO2005/123258 discloses a bioreactor for studying the effects of imposed stimuli on cellular activity.

STATEMENT OF THE INVENTION

In a first aspect of the invention there is provided a bioreactor chamber assembly comprising:
 a bioreactor chamber comprising first and second portions arranged to be coupled to one another thereby to provide a liquid-tight seal therebetween;
 a pair of clamp members; and
 a pair of resilient loop elements,
 wherein the clamp members are arranged to sandwich the chamber between the clamp members and the loop elements are arranged to apply a force between the clamp members to urge the first and second portions together.

This has the advantage that the first and second portions may be clamped together in a rapid, convenient and reliable manner.

Preferably each loop element is arranged to apply a force to each clamp member at a different respective position of each clamp member such that each loop element applies a substantially equal and opposite torque to each clamp member about an axis normal to a direction along which the force is applied between the clamp members.

Preferably the clamp members are each provided with a recessed portion arranged to receive a portion of the chamber therein.

Preferably the clamp members each comprise a substantially plate-like member.

The clamp members may be provided with one or more grip portions arranged to constrain movement of the loop elements with respect to the clamp members when the loop elements apply said force between the clamp members.

Preferably the one or more grip portions each comprise a grooved portion of a clamp member.

Preferably the one or more grip portions are provided on a side of a clamp member opposite the side on which the chamber is provided.

Preferably at least one clamp member comprises a substantially disc-shaped member.

The loop elements may each comprise an endless loop.

Optionally a pair of loop elements are provided by a single endless loop. In such an embodiment the single endless loop may be provided in a figure of 8 form. One clamp member may be adapted to accommodate a cross-over of the figure of 8 form.

The loop elements may be formed from an elastomeric material.

Preferably at least one of the clamp members is fixedly attached to a substrate.

Preferably at least one of the clamp members is provided by a substrate.

Preferably the substrate provides a clamp member of a plurality of chamber assemblies.

Preferably the first portion is a body portion of the chamber, the body portion having at least one open end, and the second portion is a basal portion of the chamber, the basal portion being arranged to provide a closure member for the at least one open end of the body portion.

Preferably the body portion has a pair of open ends, one end of the body portion being coupled to the basal portion, the opposite end being coupled to a third portion.

The third portion may have one open end and one closed end.

Preferably the first and second portions are comprised by a plurality of portions arranged to be coupled together to form the chamber, the chamber being arranged whereby one or more barriers may be provided within the chamber thereby to define a plurality of fluid reservoirs, at least one portion of the chamber having a fluid inlet aperture and a fluid outlet aperture arranged whereby fluid flow through a reservoir may be established.

Each reservoir may be associated with a different respective portion.

The one or more barriers may be provided at a location or respective locations substantially between a pair of adjacent portions.

Preferably the one or more barriers is/are provided in the form of a substantially flat sheet of material, optionally a membrane.

The one or more barriers may be arranged to allow passage of a prescribed substance therethrough.

The one or more barriers may be arranged to allow passage of a prescribed substance therethrough wherein the substance is selected from amongst a fluid; a chemical compound, moiety or element; an ion; and a biological material.

Preferably the fluid inlet aperture of at least one portion is arranged such that fluid entering a reservoir of the chamber through the inlet aperture flows in a direction substantially parallel to a plane of a barrier defining a boundary of the reservoir.

Preferably the respective portions have substantially the same cross-sectional area as one another.

Preferably respective portions are provided with one or more respective complementary formations arranged whereby the portions may be coupled to one another, the complementary formations comprising a resiliently deformable material and arranged whereby a liquid-tight seal may be formed between the respective formations without a requirement for a separate seal element.

This has the advantage that because a separate seal element (such as an 'O' ring or any other seal element) is not required, assembly of a module may be made in a more rapid and convenient manner. Furthermore, a component count of a chamber may be reduced thereby simplifying manufacture and assembly.

In addition, a compatibility of a seal element with liquid or other fluid in a chamber does not need to be verified. Thus, a usefulness of the chamber may be enhanced. A possibility of contamination of a content of a chamber due to an influence of a seal element is thereby eliminated.

Preferably the one or more formations of the first portion comprise a rim of an end of a wall of the first portion, the rim having a recess formed in a radially inner circumferential portion of the rim whereby the remaining portion of the rim defines a substantially circumferential skirt portion.

Preferably a corresponding one or more formations of the second portion comprise a corresponding portion of a rim of an end of a wall of said second portion, the wall having a recess formed in a radially outer circumferential portion whereby the remaining portion of the wall defines a skirt portion having a shape and size complementary to that of the skirt portion of the first portion.

The first and second portions may be arranged to allow a membrane to be coupled between them by entrapment of a portion of the membrane between respective adjacent rims of the first and second portions.

The chamber may be arranged whereby entrapment of a membrane may be effected when adjacent portions are coupled to one another.

The portions may be releasably coupled to one another.

The fluid inlet aperture and fluid outlet aperture of the at least one portion may be provided at substantially opposite locations of the wall of the chamber.

The chamber may be substantially cylindrical in shape.

Preferably each portion of the chamber is substantially cylindrical in shape, the portions being arranged to be coupled together in a substantially coaxial configuration.

Preferably the inlet aperture and the outlet aperture are provided at diametrically opposite locations of each portion.

Preferably the chamber comprises a portion not having a fluid inlet aperture or a fluid outlet aperture.

Preferably the assembly is further provided with a sample support arranged to support a sample in the form of a membrane, the support being arranged to allow each of a pair of opposed major faces of the membrane to be exposed to fluid contained within the chamber.

Preferably the sample support comprises at least one support member arranged to contact a portion of the sample.

The at least one support member may comprise a ridged element, the ridged element being elongate in a substantially lateral direction thereby to provide an elongate surface upon which a sample may be placed.

Preferably the at least one support member comprises at least one post element.

Preferably the at least one post element is provided with an upper surface arranged to contact a sample, the upper surface being one selected from amongst substantially flat, substantially curved and substantially domed.

The at least one support member may comprise an element substantially in the form of a hemisphere or portion thereof.

Preferably the sample support comprises a plurality of support members each support member being arranged to contact a portion of the sample.

The plurality of support members may be arranged substantially parallel to one another.

The support members may be of substantially square or rectangular cross-section.

The basal portion may have a hollow, cupped body portion.

Preferably the basal portion is arranged to receive a sample therein.

Preferably the sample support is provided in the basal portion.

The portions may be arranged to couple to one another at least in part by means of a friction fit.

Preferably the complementary formations are formed from a material having a self-adhesive property.

Preferably respective complementary formations are arranged to form a bond with one another.

The bond may be a releasable bond.

Alternatively the bond may be a substantially permanent bond.

Preferably the complementary formations of a portion and a remainder of the portion are formed from substantially the same material.

Preferably the one or more respective complementary formations of a portion are integrally formed with the portion.

The complementary formations may be formed from a silicone material.

Preferably at least one portion comprises a substantially transparent or translucent material thereby to allow light to irradiate a sample provided within the chamber.

In a second aspect of the invention there is provided a bioreactor chamber assembly comprising:
  a chamber comprising a plurality of modules arranged to be coupled together to form the chamber, the chamber being arranged whereby one or more barriers may be provided within the chamber thereby to define a plurality of fluid reservoirs, at least one module of the chamber having a fluid inlet aperture and a fluid outlet aperture arranged whereby fluid flow through a reservoir may be established,
  wherein respective modules are provided with one or more respective complementary formations arranged whereby the modules may be coupled to one another, the complementary formations comprising a resiliently deformable material and arranged whereby a liquid-tight seal may be formed between the respective formations without a requirement for a separate seal element.

This has the advantage that because a separate seal element (such as an 'O' ring or any other seal element) is not required, assembly of a module may be made in a more rapid and convenient manner. Furthermore, a component count of a chamber may be reduced thereby simplifying manufacture and assembly.

In addition, a compatibility of a seal element with liquid or other fluid in a chamber does not need to be verified. Thus, a usefulness of the chamber may be enhanced. A possibility of contamination of a content of a chamber due to an influence of a seal element is thereby eliminated.

It is noted that the modules may correspond to the portions of the first aspect of the invention.

Each reservoir may be associated with a different respective module.

Preferably the barrier is provided at a location substantially between a pair of adjacent modules.

The assembly may be arranged wherein the barrier is provided in the form of a substantially flat sheet of material.

Preferably the barrier is arranged to allow passage of a prescribed substance therethrough.

Preferably the barrier is arranged to allow passage of a prescribed substance therethrough wherein the substance is selected from amongst a fluid; a chemical compound, moiety or element; an ion; and a biological material.

The assembly may be arranged wherein the fluid inlet of the at least one module is arranged such that fluid entering a reservoir of the chamber through the inlet aperture flows in a direction substantially parallel to a plane of a barrier defining a boundary of the reservoir.

Preferably the modules have substantially the same cross-sectional area as one another.

Preferably the modules may be releasably coupled to one another.

Preferably the one or more formations of a first module comprise a rim of an end of a wall of the first module, the rim having a recess formed in a radially inner circumferential portion of the rim whereby the remaining portion of the rim defines a substantially circumferential skirt portion.

Preferably a corresponding one or more formations of a second module comprise a corresponding portion of a rim of an end of a wall of said second module, the wall having a recess formed in a radially outer circumferential portion whereby the remaining portion of the wall defines a skirt portion having a shape and size complementary to that of the skirt portion of the first module.

The first and second modules may be arranged to allow a membrane to be coupled between them by entrapment of a portion of the membrane between respective adjacent rims of the first and second modules.

Preferably the assembly is arranged whereby entrapment of a membrane may be effected when adjacent modules are coupled to one another.

Preferably the fluid inlet aperture and fluid outlet aperture of the at least one module are provided at substantially opposite locations of the wall of the chamber.

Preferably the chamber is substantially cylindrical in shape.

Preferably each module is substantially cylindrical in shape, the modules being arranged in a substantially coaxial configuration.

Preferably the inlet aperture and the outlet aperture are provided at diametrically opposite locations of each module.

Preferably the assembly comprises a module not having a fluid inlet aperture or a fluid outlet aperture.

Preferably the assembly is further provided with a sample support arranged to support a sample in the form of a membrane, the support being arranged to allow each of a pair of opposed major faces of the membrane to be exposed to fluid contained within the chamber.

Preferably the sample support comprises at least one support member arranged to contact a portion of the sample.

Preferably the at least one support member comprises a ridged element, the ridged element being elongate in a substantially lateral direction thereby to provide an elongate surface upon which a sample may be placed.

Preferably the at least one support member comprises at least one post element.

Preferably the at least one post element is provided with an upper surface arranged to contact a sample, the upper surface being one selected from amongst substantially flat, substantially curved and substantially domed.

Preferably the at least one support member comprises an element substantially in the form of a hemisphere or portion thereof.

Preferably the sample support comprises a plurality of support members each support member being arranged to contact a portion of the sample.

Preferably the plurality of support members are substantially parallel to one another.

The support members may be of substantially square or rectangular cross-section.

Preferably a cap module is provided comprising a module arranged to define a closed end of the chamber.

Preferably the cap module has a hollow, cupped body portion.

The cap module may be arranged to receive a sample therein.

Preferably the sample support is provided in the cap module.

A further cap module may be provided at an opposite end of the chamber to said cap module.

Preferably the modules are arranged to couple to one another at least in part by means of a friction fit.

Preferably the complementary formations are formed from a material having a self-adhesive property.

Respective complementary formations may be arranged to form a bond with one another.

The bond may be a releasable bond.

Alternatively the bond may be a substantially permanent bond.

The complementary formations and a remainder of the modules may be formed from substantially the same material.

Preferably the one or more respective complementary formations of a module are integrally formed with the module.

The complementary formations may be formed from a silicone material.

Preferably at least one module comprises a substantially transparent or translucent material thereby to allow light to irradiate a sample provided within the chamber.

In a third aspect of the invention there is provided bioreactor apparatus comprising a plurality of bioreactor chamber assemblies according to the second aspect wherein a first reservoir of a first chamber assembly is coupled to a first reservoir of a second chamber assembly.

The first reservoirs of the first and second chambers may be coupled in series whereby fluid may be caused to flow through the first reservoir of the first chamber and subsequently through the first reservoir of the second chamber.

Alternatively the first reservoirs of the first and second chambers may be coupled in parallel.

BRIEF DESCRIPTION OF THE DRAWINGS

Embodiments of the invention will now be described with reference to the accompanying figures in which.

DETAILED DESCRIPTION

Figure 1:
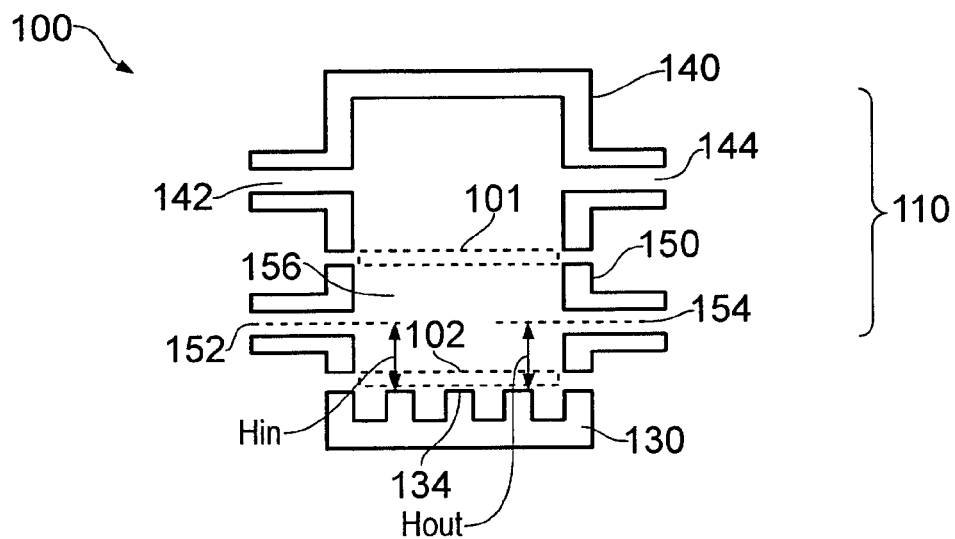
FIG. 1 is a cross-sectional view of a chamber suitable for use in dual-cavity (or 'dual-reservoir') perfusion experiments.

FIG. 1 shows a chamber 100 for a bioreactor according to an embodiment of the invention. The chamber 100 has a body portion 110 having a cap module 140 and a body module 150. The cap module 140 and body module 150 are each provided with an inlet aperture 142, 152 and an outlet aperture 144, 154 respectively.

The cap and body modules 140, 150 are arranged to couple together whereby a fluid-tight seal is formed between the modules.

Figure 2:
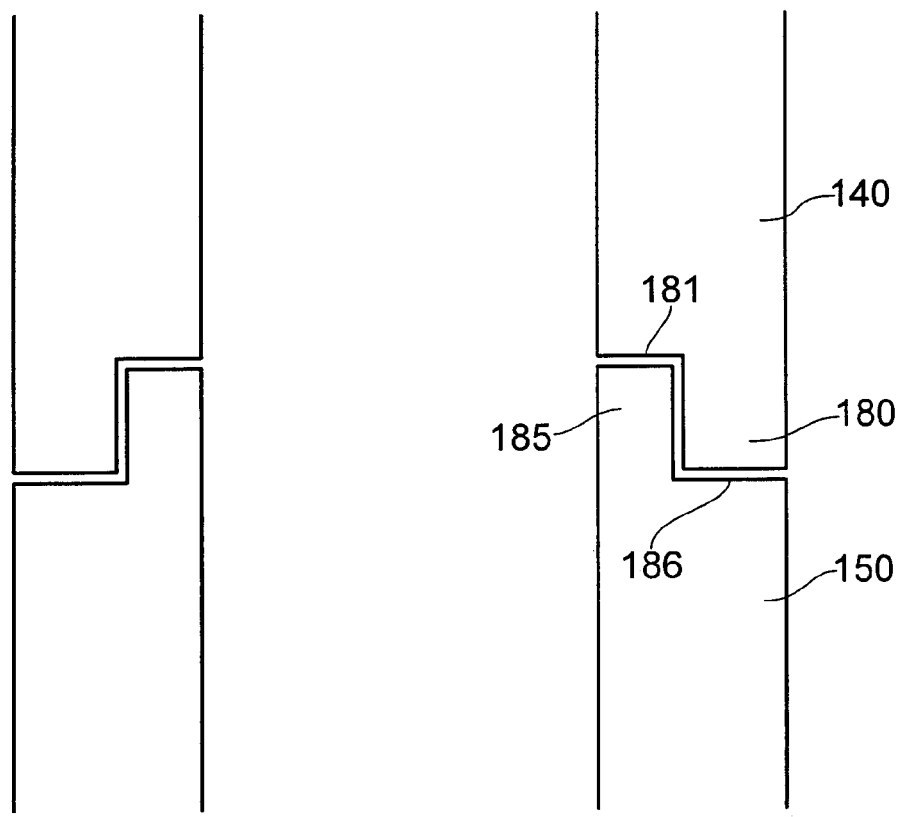
FIG. 2 is a cross-sectional view of rim portions of adjacent modules of the chamber of FIG. 1 showing complementary formations by means of which the modules may be coupled together.

FIG. 2 shows a configuration of the structure of the coupling between the cap and body modules 140, 150. It can be seen that rims 180, 185 of the cap and body modules 140, 150 respectively are provided with complementary formations. Thus, a rim 180 of the cap module 140 is provided with a recessed portion 181 along a radially inner circumferential edge of the rim 180 whilst a rim 185 of the body module 150 is provided with a recessed portion 186 along a radially outer circumferential edge. Skirt portions defied by respective remaining portions of rims 180, 185 are of a shape complementary to one another allowing coupling of the chambers together.

In some embodiments the complementary formations are arranged to provide a friction fit.

Figure 3:
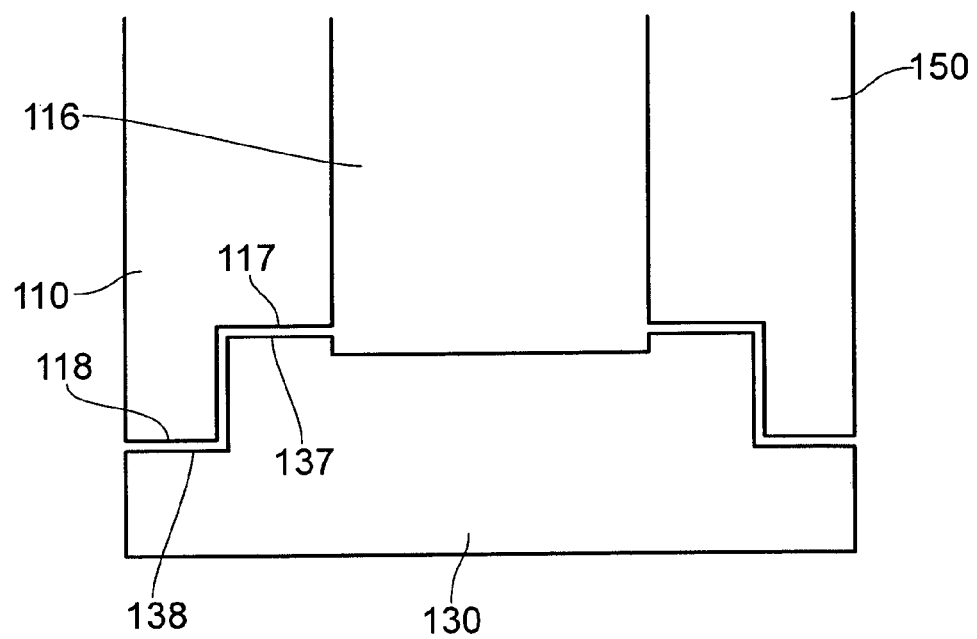
FIG. 3 is a cross-sectional view of a configuration of a coupling between a basal portion of the chamber and a body module.

FIG. 3 shows a configuration of the structure of the coupling between the body module 150 of the chamber 100 and a basal portion 130. It can be seen that similar formations are provided to those allowing the cap and body modules 140, 150 to be coupled together. In other words, a rim 118 of the body module 150 is provided with a recess 117 of a shape corresponding to that of a recess 138 formed in a rim 137 of the basal portion 130.

In some embodiments the basal portion 130 is formed from the same type of material as the cap and body modules 140, 150. Thus in some embodiments the basal portion 130 is formed from a silicone rubber. Other materials are also useful.

Figure 4:
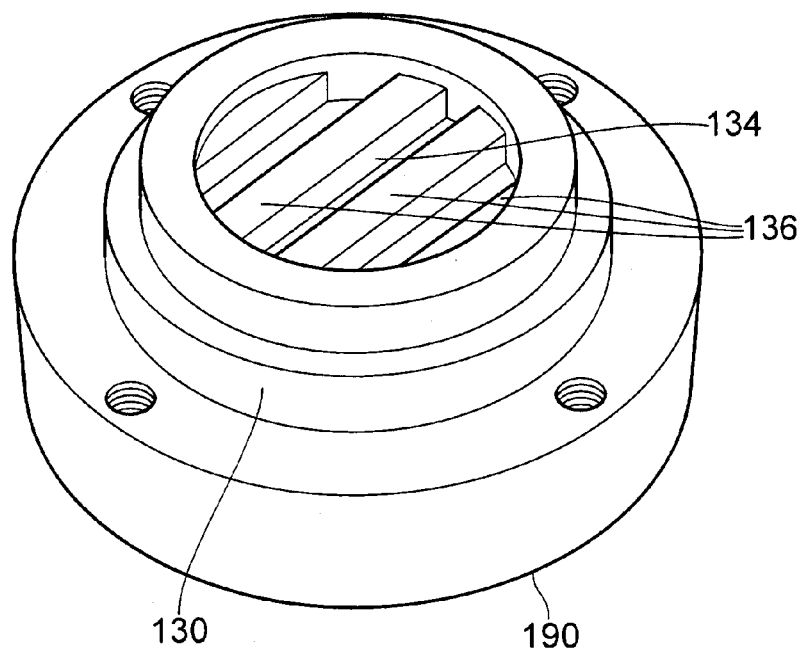
FIG. 4 is a perspective view of a basal portion also showing a lower clamping plate.

FIG. 4 shows a perspective view of a basal portion 130 formed from silicone rubber. The basal portion 130 is shown mounted on a clamping plate 190. A corresponding clamping plate (not shown) is also provided that is arranged to be placed in abutment with the cap module 140 of the chamber 100. The two clamping plates are then clamped together in order to enhance a fluid-tightness of a seal between the modules. Clamping also enables the chamber 100 to withstand greater internal pressure without suffering undue deformation.

Figure 5:
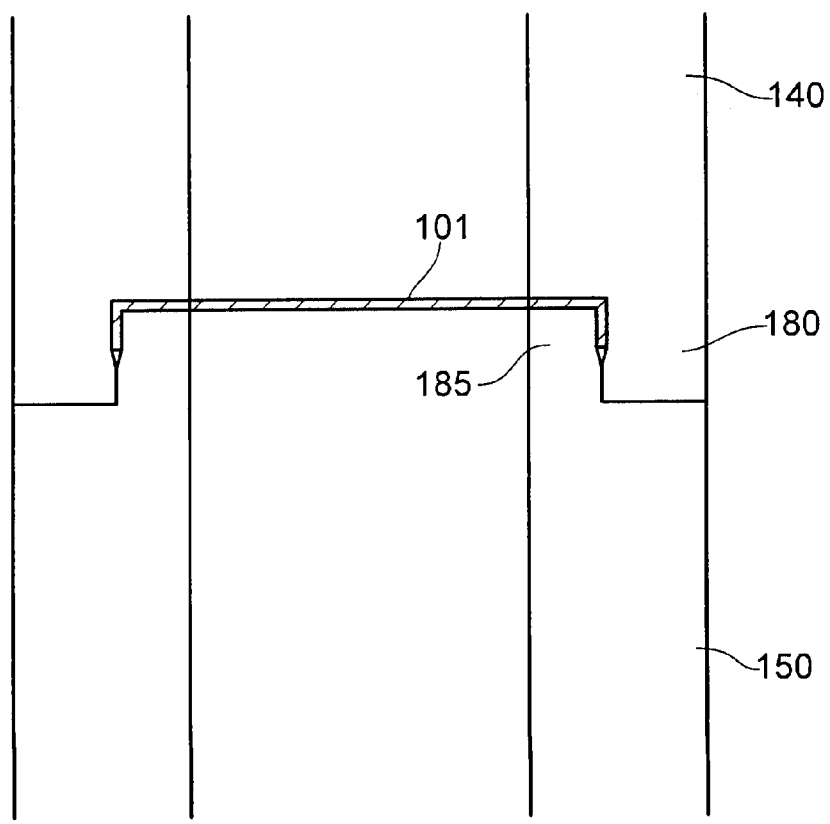
FIG. 5 is a cross-sectional view of rim portions of adjacent modules showing how a membrane may be gripped between adjacent modules.

As illustrated in FIG. 5, the chamber 100 is configured to allow a first sample 101 in the form of a membrane 101 to be supported between the cap and body modules 140, 150 whereby a barrier to fluid flow between the cap and body modules 140, 150 may be formed. The membrane may be arranged to provide a molecularly selective filter. The membrane may allow diffusion or perfusion of molecules or other entities therethrough, including fluids or any required material. The membrane may in addition or instead provide a support for cells or other matter.

In the arrangement of FIG. 5 the membrane 101 is supported by being trapped between rims 180, 185 of the cap and body modules 140, 150 when the cap and body modules 140, 150 respectively are coupled together. Other methods of supporting the membrane 101 between the cap and body modules 140, 150 are also useful.

It will be understood that clamping of modules together using a clamping plate 190 or other mechanism can beneficially increase a force trapping the sample 101 between rims 180, 185.

In some embodiments of the invention the body portion 110 and the basal portion 130 are formed from a resiliently flexible material such as a polymeric material. In some embodiments the portions 130, 110 are formed from a silicone material. In some embodiments the portions 130, 110 are formed from a transparent material whereby a sample within the chamber 100 may be subjected to irradiation with visible, infra-red and/or ultraviolet light through one or both of the portions 130, 110.

As can be seen in FIG. 4 the basal portion 130 of the chamber 100 has a sample support portion 134 having a plurality of spaced apart ridge elements 136. The ridge elements 136 are arranged to support a second sample 102 in such a manner that fluid within an internal cavity (or 'reservoir') 156 of the body module 150 of the chamber 100 is able to contact the second sample 102 on a face of the sample 102 that is towards the sample support portion 134 as well as an opposite face of the sample.

This feature reduces a risk that a tissue sample will experience necrosis on the face that is towards the sample support portion 134. Furthermore, this feature also facilitates removal of a sample 102 placed on the support portion 134. If the sample 102 is placed in contact with a substantially flat surface the effects of surface tension can render the task of removing the sample 102 from the support portion 134 difficult. In such situations, samples such as thin membranes or glass cover-slips can otherwise become damaged during a process of removal.

It is to be understood that other means for supporting a sample may be provided, such as a plurality of polygonal protrusions such as triangular, square or rectangular protrusions, or circular, spherical protrusions or protrusions of any other suitable shape.

Whilst the embodiment of FIG. 4(a) is provided with ridge elements, it is to be understood that in some other embodiments one or more post elements may be provided. FIG. 4(b) shows an embodiment in which post elements are provided in the form of rectangular cuboids 137 whilst FIG. 4(c) shows an embodiment in which post elements are provided in the form of domed elements 138. Other shapes are also useful. In some embodiments one or more domed formations may be provided.

The chamber 100 is arranged to allow two separate fluid flowpaths to be established therethrough when a barrier such as a sample 101 in the form of a membrane is provided between the cap and body modules 140, 150. A first flowpath is arranged from the inlet aperture 142 to the outlet aperture 144 of the cap module 140. A second flowpath is arranged from the inlet aperture 152 to the outlet aperture 154 of the body module 150.

In some embodiments, a flow of fluid or other substances between the cap and body modules 140, 150 is constrained to occur by transport through the sample 101.

It is to be understood that locations and sizes of the inlet aperture 142 and outlet aperture 144 of the cap module 140 and/or the locations of the inlet aperture 152 and outlet aperture 154 of the body module in the embodiment of FIG. 1 may be arranged so as to minimise or at least reduce a deleterious effect of the fluid flow on samples 101 and/or 102, respectively.

For example, in some embodiments cell seeding or other phenomena may be arranged to occur on the second sample 102, the first sample 101 being a membrane arranged to allow perfusion of fluid and/or certain molecules or other entities therethrough. Limiting a deleterious effect of the flow of fluid through the body module 150 on the growth, function and/or viability of cellular or other material on the second sample 102 may be an important factor in establishing suitable conditions.

In some embodiments the outlet aperture of a module is arranged to be of a larger diameter than the inlet aperture of the module. In some embodiments the outlet aperture is greater than the inlet aperture by a factor of around 1.5 or more. In some embodiments the outlet aperture is greater than the inlet aperture by a factor of around 2 or more.

The present inventors have determined that the height $H_{in}$ of the inlet aperture 152 above the support portion 134 and the height $H_{out}$ of the outlet aperture 154 above the support portion 134 (FIG. 1) are factors that influence the fluid flow conditions at the support portion 134.

The inventors have recognised that heights $H_{in}$ and $H_{out}$ may be arranged to provide an optimum balance between larger values of $H_{in}$ and $H_{out}$ in order to achieve a reduced amount of shear stress on an upper surface of the second sample 102, and smaller values of $H_{in}$ and $H_{out}$ in order to avoid an excessive amount of turbulent flow at the sample surface. The heights of the inlet and outlet apertures 142, 144 of the cap module 140 above the first sample 101 may also be selected so as to provide a balance between an amount of shear stress imposed on the sample 101 by flow of fluid through the cap module 140 and an extent to which flow of fluid through the cap module 140 occurs under laminar flow conditions. The heights may also be arranged to reduce or prevent depletion of oxygen or nutrients at the sample.

Figure 6:
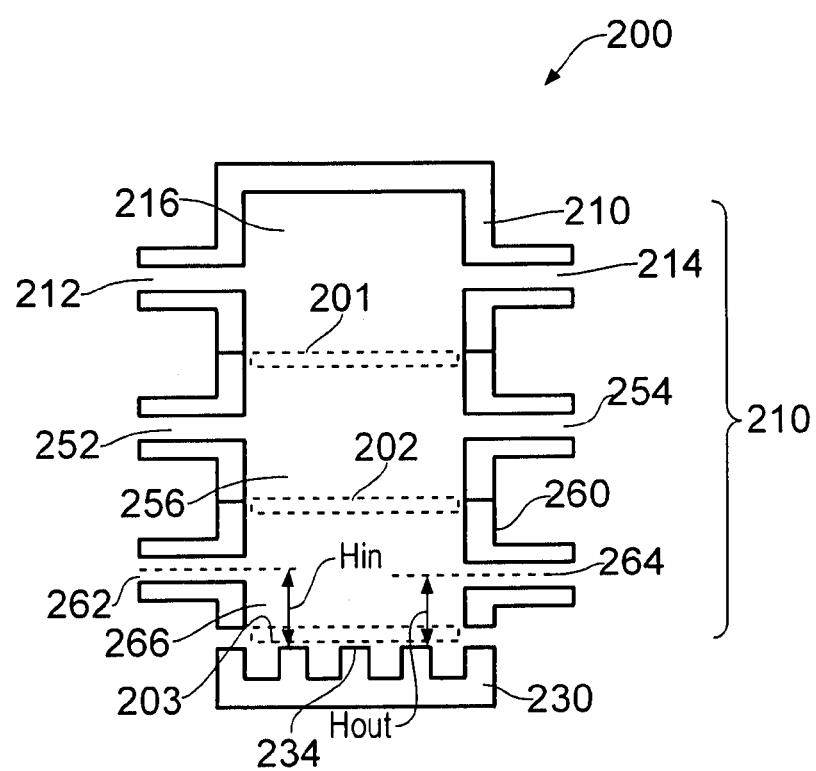
FIG. 6 is a cross-sectional view of a chamber suitable for use in triple-cavity perfusion experiments.

FIG. 6 shows an embodiment of the invention in which a chamber 200 similar to that of FIG. 1 is provided, the chamber 200 having a cap module 210 that is substantially the same as that of the chamber 100 of FIG. 1 and first and second body modules 250, 260 each substantially identical to the body module 150 of the embodiment of FIG. 1.

In the embodiment of FIG. 6 the first and second body modules 250, 260 are stacked on top of one another such that the body portion 210 has first, second and third internal cavities 216, 256, 266.

The first and second internal cavities 216, 256 are arranged to be separated from one another by means of a first sample 201 whilst the second and third internal cavities 256, 266 are arranged to be separated from one another by means of a second sample 202. A third sample 203 may be provided on a support portion 234 provided by the basal portion 230.

In some embodiments the first and second samples 201, 202 are membranes arranged to allow diffusion of required substances therethrough whilst the third sample 203 is a sample upon which cellular seeding is arranged to occur.

A flow of fluid may be established independently through each of the first, second and third internal cavities 216, 256, 266 respectively. Respective inlet and outlet apertures 212, 214 (first cavity), 252, 254 (second cavity) and 262, 264 (third cavity) are provided to facilitate the flow of fluid through the respective cavities.

For the reasons discussed above in relation to the embodiment of FIG. 1, the heights $H_{in}$ and $H_{out}$ of inlet aperture 262 and outlet aperture 264 of the third cavity 266 may be arranged to provide an optimum balance between an amount of shear stress imposed on an upper surface of the third sample 203 and an extent to which flow of fluid over the third sample 203 is turbulent. The heights may also be arranged to reduce or prevent depletion of oxygen or nutrients at the sample.

Similarly, the heights of the inlet and outlet apertures of the cap module 210 and first body module 250 above first and second samples 201, 202 may also be adjusted to provide an optimum balance between the amount of shear stress imposed on the samples 201, 202 due to fluid flow through the modules 210, 250 and an extent to which flow of fluid at the surface of the samples 201, 202 is turbulent. The heights may also be arranged to reduce or prevent depletion of oxygen or nutrients at the sample.

It is to be understood that due to the modular nature of the chamber 200, a chamber 200 with substantially any number of body modules 250, 260 may be provided as required for any given application. In some embodiments body modules 250, 260 are substantially identical components.

Figure 7:
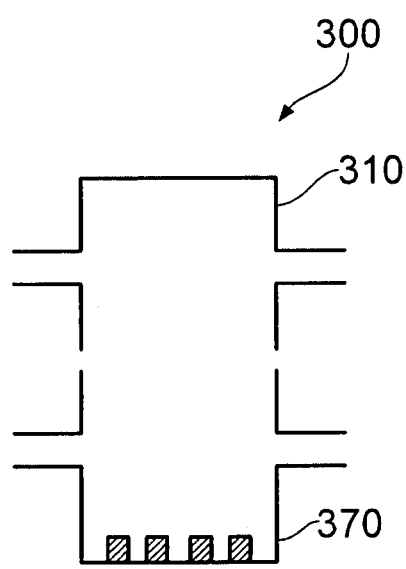
FIG. 7 is a cross-sectional view of a chamber according to a further embodiment of the invention.

FIG. 7 shows an embodiment of the invention in which a basal module 370 is provided instead of a basal portion 130 (FIG. 1). In the embodiment of FIG. 7 the basal module 370 may be considered to be a combination of a body module 150 and a basal portion 130 of the embodiment of FIG. 1, the basal module 330 being provided in the form of a single module 370. A basal module 370 according to the embodiment of FIG. 7 has the advantage that a risk of fluid leaks from a seal formed between a body module 150 and a basal portion 130 of the embodiment of FIG. 1 is reduced.

It is to be understood that in some variations of the embodiment of FIG. 7 one or more body modules 150 may be coupled between the cap module 310 and basal module 370 of the embodiment of FIG. 7.

Figure 8:
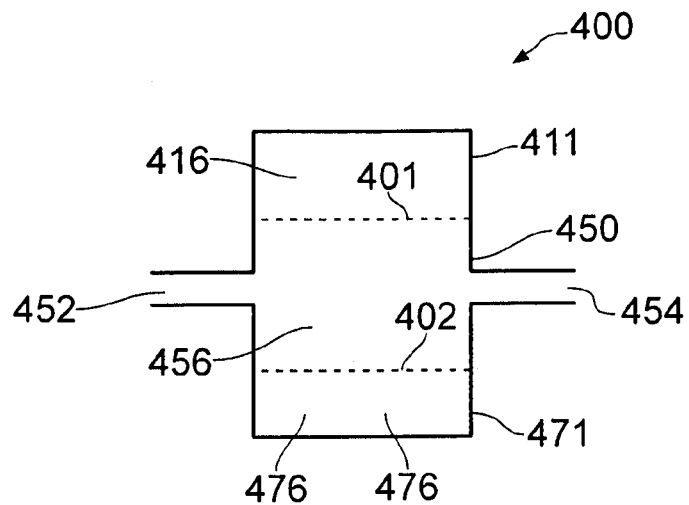
FIG. 8 shows a chamber according to an embodiment of the invention.

FIG. 8 shows a chamber 400 in which a cap module 411 and a basal module 471 are provided not having inlet apertures or outlet apertures. The cap module 411 is coupled to a body module 450 which is in turn coupled to the basal module 471 such that the body module 450 is sandwiched between the cap and basal modules 411, 471. The body module 450 is provided with inlet and outlet apertures 452, 454 arranged to allow passage of fluid through the module 450.

A membrane 401 provides a barrier between an internal cavity 416 of the cap module 411 and an internal cavity 456 of the body module 450. A membrane 402 provides a barrier between the internal cavity 456 of the body module 450 and an internal cavity 476 of the basal module 471.

In the embodiment of FIG. 8 a supply of fluid may be provided in the internal cavities 416, 476 of the cap and basal modules 411, 471. A chamber 400 according to the embodiment of FIG. 8 can allow simulation of biological tissue that is fed by surrounding capillaries. Thus, for example tissue samples may be provided in one or both of the cap and basal modules 411, 471 and a supply of fluid passed through the body module 450, the fluid passing through the body module 450 being arranged to simulate a flow of blood through capillaries associated with the biological tissue. The biological tissue may be provided on a sample support of one or both of the cap and basal modules 411, 471. Alternatively or in addition the biological tissue may be provided on one or both of the membranes 401, 402, for example on a side facing into the cavity of a respective cap or basal module 411, 471.

Figure 9:
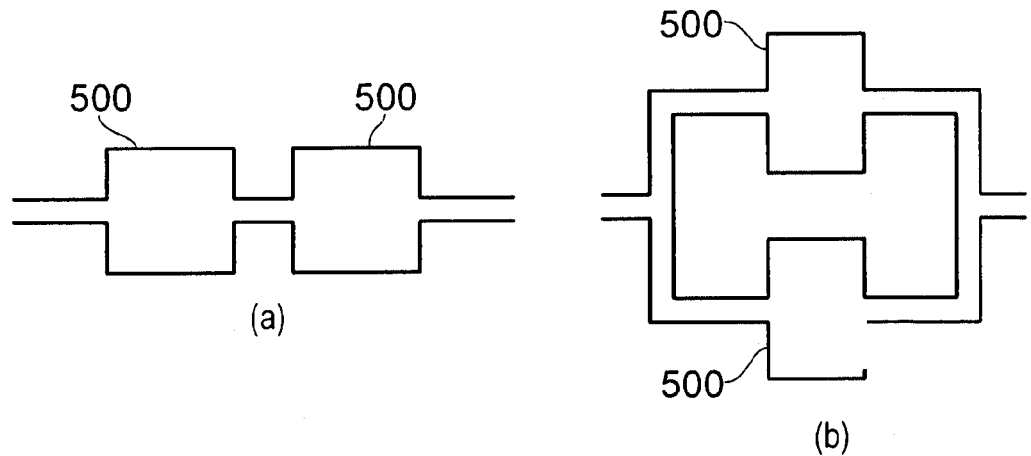
FIG. 9(a) to (c) show assemblies of chambers according to embodiments of the invention.

FIG. 9(a) shows an embodiment in which chambers 500 according to embodiments of the invention are coupled together in series to form an assembly of chambers. A corresponding assembly of chambers 500 coupled in parallel is shown in FIG. 9(*b*).

FIG. 9(*c*) shows an assembly of chambers in which a first chamber 600A has a basal module 671 having no inlet or outlet aperture, the basal module 671 being coupled to a cap module 610 having an inlet aperture and an outlet aperture 612, 614. A membrane 601A is provided between the cap module and the basal module of the first chamber 600A.

The cap module of the first chamber 600A is coupled to a cap module 610 of a second chamber 600B, the cap module of the second chamber 600B being similar to that of the first chamber 600A in that it is also provided with an inlet aperture 612 and an outlet aperture 614.

The cap module 610 of the second chamber 600B is coupled to a basal module 670 of the second chamber also having an inlet aperture 672 and an outlet aperture 674. A sample 601B in the form of a membrane is provided between the cap module 610 and the basal module 670. A further sample may be provided on a sample support of the basal module 670 of the second chamber, the basal module 671 of the first chamber, or any other module of the first or second chambers 600A, 600B.

It is to be understood that by suitable choice of chamber configuration by assembly of modules of different respective types a bioreactor may be formed suitable for the simulation of highly complex biological processes.

Embodiments of the present invention provide a highly effective way of providing such bioreactors, allowing a user a very high degree of flexibility in choice of reactor configuration and an ability to make modifications and adjustments in a rapid and efficient manner.

In the embodiment shown in the figures the cap, body and basal modules and the basal portion are arranged to couple to one another at least in part by means of a friction fit, allowing releasable coupling to one another in a convenient manner not requiring special tools. The modules and portion are formed from a silicone rubber material, being a resiliently deformable material having a self-adhesive property. This promotes the formation of a substantially water-tight joint between modules and/or between a module and the basal portion.

In the embodiment shown the silicone rubber is formed to be substantially transparent to light, allowing exposure of cells within a chamber 100, 200, 300 to be exposed to light to test an influence of visible (or infra-red) light on cell function.

It is to be understood that other materials and forms of material are also useful for forming the modules and basal portion.

It will be apparent to persons skilled in the art that one or more modules and the basal portion may be formed by moulding. Other methods of forming the modules and basal portion are also useful.

Figure 10A:
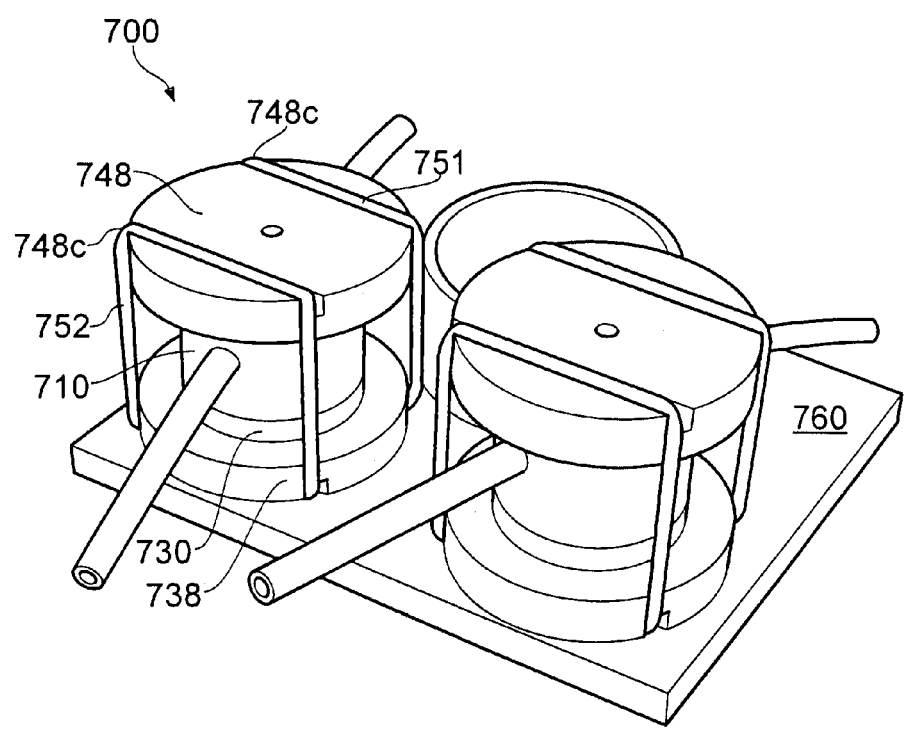
FIG. 10 shows a chamber assembly according to an embodiment of the invention in which a chamber is sandwiched between two clamp members in (a) perspective view and (b) cross-sectional view.
Figure 10B:
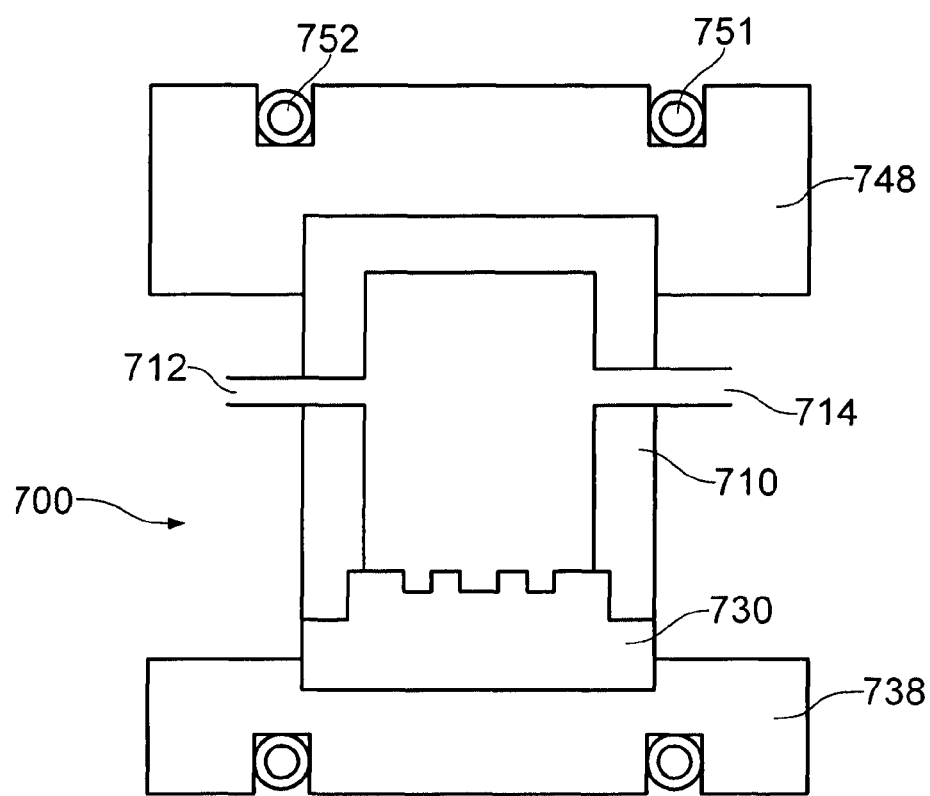

FIG. 10(*a*) shows an embodiment of the invention having a pair of clamp members 738, 748 arranged to sandwich a basal portion 730 and a body portion 710 of a chamber 700 therebetween. The embodiment of FIG. 10(*a*) shows two chambers 700 so arranged. It is to be understood that in some embodiments only one chamber 700 is provided. The embodiment of FIG. 10(*a*) also shows the two chambers 700 in a configuration in which one clamp member 738 is provided on a substrate 760. In some embodiments the clamp member 738 is coupled to the substrate 760. In some embodiments no substrate 760 is provided.

FIG. 10(*b*) is a cross-sectional view of one of the chambers 700 shown in the embodiment of FIG. 10(*a*).

Figure 11A:
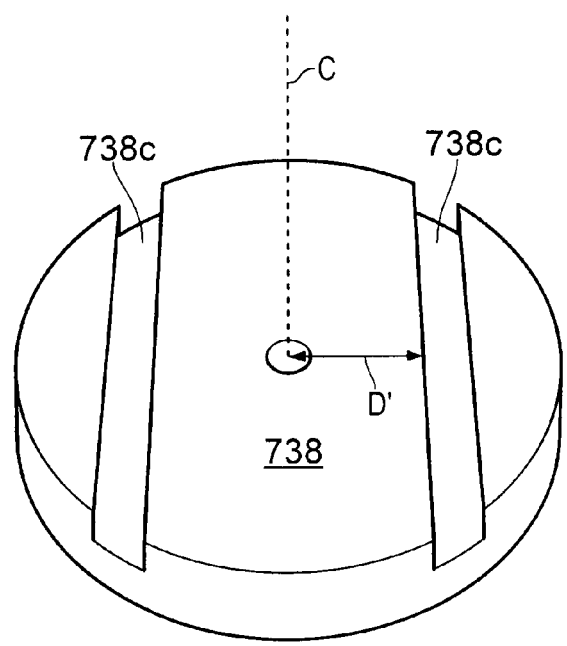
FIG. 11 shows (a) an outer surface and (b) an inner surface of a clamp member according to an embodiment of the invention.
Figure 11B:
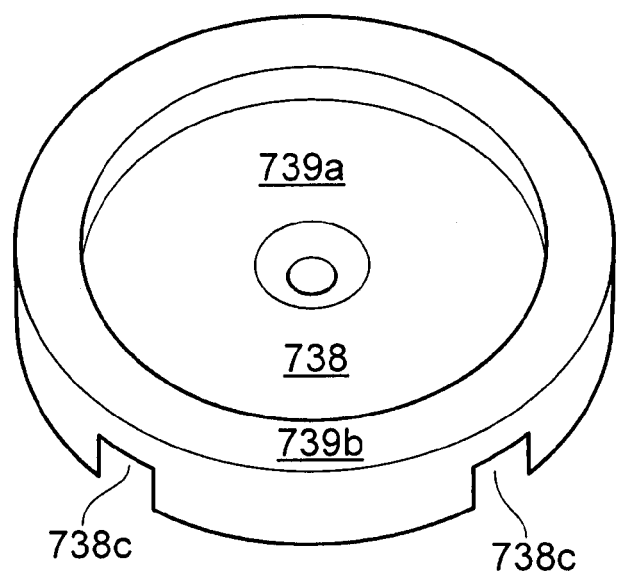

In some embodiments the clamp members 738, 748 are substantially identical. As can be seen from FIG. 10 and FIG. 11 the clamp members 738, 748 are in the form of disc-like members each having a side having a recessed well portion 739*a* and a corresponding rim portion 739*b* (FIG. 11(*b*)). The well portion 739*a* of one clamp member 738 is sized to receive a portion of the basal portion 730 of the chamber therein.

The other clamp member 748 has a corresponding recessed well portion arranged to receive a portion of the body portion 710 therein.

Thus in some embodiments the chamber 700 is arranged to be locatable between the clamp members 738, 748 whereby lateral movement of the clamp members with respect to the chamber 700 is constrained by the presence of the rim portions 739*b*.

In order to provide a clamping force between the clamp members 738, 748, in the embodiment of FIGS. 10 to 13 a pair of resilient elements are provided in the form of endless loops 751, 752. The clamp members 738, 748 are provided with recessed channels 738*c* on an outer major surface thereof (being the surface opposite the surface in which the well portion 739*a* is provided). In the embodiment shown the recessed channels 738*c* are substantially parallel to one another and are provided at locations disposed equal distances D' from a longitudinal axis L of the disc element 738, 748 but on opposite sides of the axis L. Thus, distance D' is a radial distance of the closest point of channel 738*c* to the axis L. In some embodiments where the clamp member 738 is a disc-like member distance D' is around two thirds of a radius of the clamp member 738. Other distances are also useful.

Figure 12:
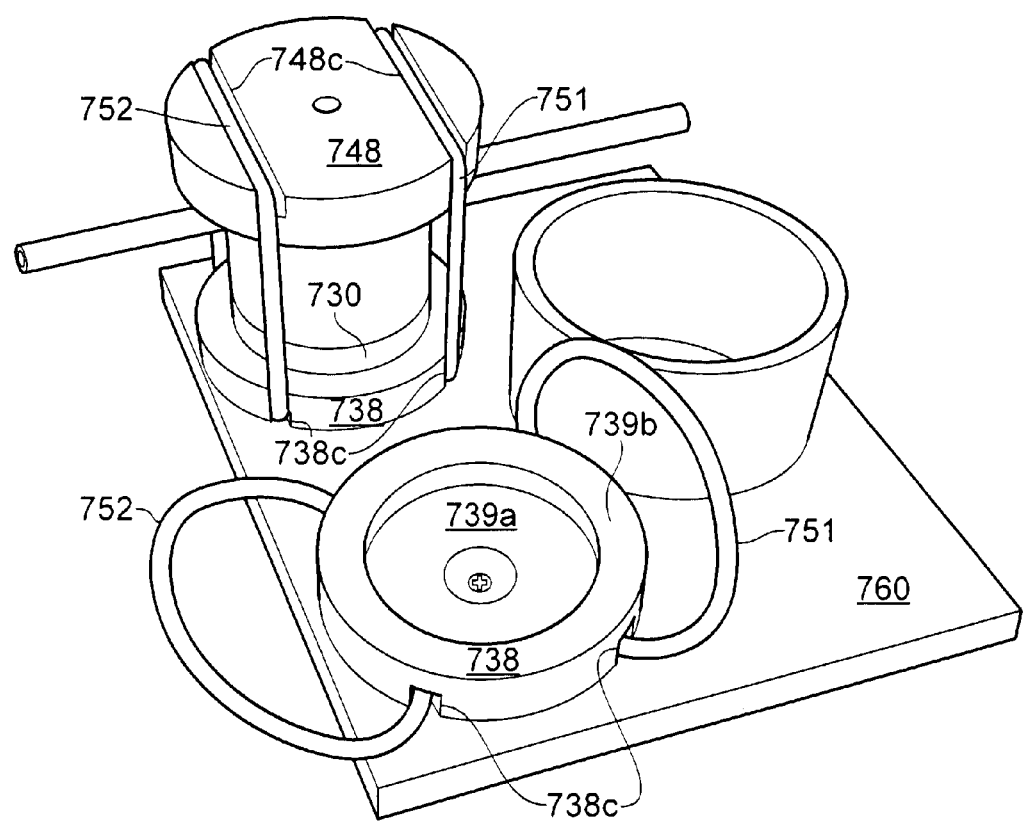
FIG. 12 is a perspective view of a substrate having a pair of clamp members fixedly coupled thereto to which respective chambers may be attached.
Figure 13:
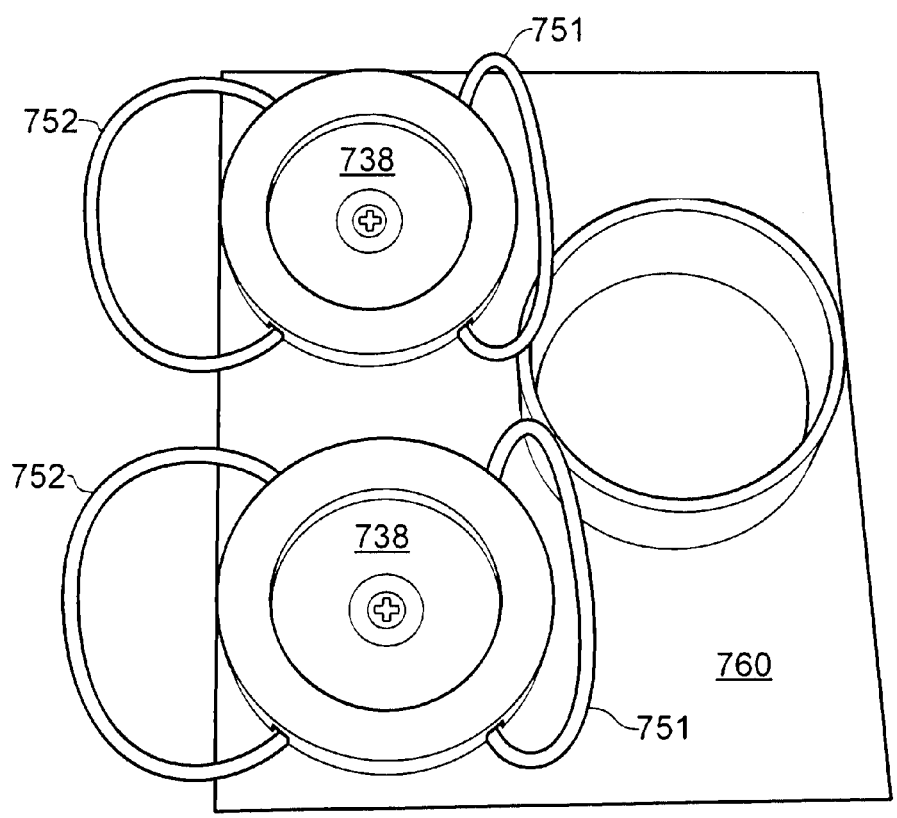
FIG. 13 is a plan view of the embodiment of FIG. 12.

In the embodiment of FIGS. 12 and 13 a lower clamp member 738 is coupled to a substrate 760 trapping the loops 751, 752 to lie within their respective channel 738*c*. The lower clamp member 738 may be coupled to the substrate 760 by permanent fixing means such as an adhesive or by means of releasable fixing means. The releasable fixing means may be a mechanical fixing element such as a screw or bolt, hook and loop fixing means (e.g. Velcro®), a releasable adhesive or any other suitable releasable fixing means.

It can be seen from FIG. 12 that a clamp member 748 (an upper clamp member) is positioned over the chamber with channels 748*c* of the upper clamp member 748 substantially parallel to those of the lower clamp member 738. The endless loops 751, 752 are sized such that they can be positioned so as to lie in respective channels 748*c* of the upper clamp member 748. The endless loops are arranged to exert a sufficient force to clamp the body portion 710 and basal portion 730 of the chamber 700 together to prevent leakage of fluid from the chamber through a joint between the body and basal portions 710, 730.

Embodiments such as that of FIGS. 10 to 13 have the advantage that a substantially equal clamping force may be applied by respective resilient elements 751, 752 at substantially equal distances either side of the longitudinal axis L of the chamber 700. Thus, clamping forces applied to the chamber 700 are balanced and a stable clamping arrangement may be provided.

It is to be understood that this has the effect that a torque applied to a clamping member 738, 748 by one resilient element 751, 752 is arranged to act in an opposite direction and to be of substantially equal magnitude to a torque applied by the other resilient element 751, 752. Thus a twisting force on the respective clamp members 738, 748 is substantially zero. This has the advantage discussed above that a stability of the assembly is enhanced.

Furthermore a chamber 700 clamped between clamp members 738, 748 is subject to substantially uniform pressure by the clamp members 738, 748. This has the advantage that a seal between the body portion 710 and basal portion 730 is also subject to uniform pressure by the clamp members 738, 748 reducing a risk of leakage of fluid.

In some embodiments, resilient elements other than endless loops are provided. In some embodiments the resilient elements are in the form of resiliently extensible linear elements. The linear elements may be flexible elements, such as lengths of an elastomer. The linear elements may be provided with one or more hook elements to facilitate coupling of the linear elements to a clamp member.

It is to be understood that in some embodiments the lower and upper clamp members 738, 748 may be formed integrally with basal and body portions of the chamber. Alternatively the lower and upper clamp members 738, 748 may be permanently coupled to basal and body portions of the chamber. In some embodiments the lower and upper clamp members 738, 748 are releasably coupled to basal and body portions of the chamber.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

The invention claimed is:

1. A bioreactor chamber assembly comprising:
a chamber comprising a plurality of modules arranged to be coupled together to form the chamber, the chamber being arranged wherein one or more barriers are provided within the chamber to define a plurality of fluid reservoirs, at least one module of the chamber having a fluid inlet aperture and a fluid outlet aperture arranged to establish fluid flow through a reservoir,
wherein respective modules are provided with one or more respective complementary formations arranged such that the modules are configured to be coupled to one another, the complementary formations comprising a resiliently deformable material and arranged to form a liquid-tight seal between the respective formations without a requirement for a separate seal element;
wherein the complementary formations comprise a first generally planar surface feature on a first module of the plurality of modules that interacts with a corresponding second generally planar surface feature on a second module of the plurality of modules such that the first and second generally planar surface features are sufficiently resiliently deformable so as to form a liquid-tight seal.

2. An assembly as claimed in claim 1 wherein the fluid inlet of the at least one module is arranged such that fluid entering a reservoir of the chamber through the inlet aperture flows in a direction substantially parallel to a plane of a barrier defining a boundary of the reservoir.

3. An assembly as claimed in claim 1 wherein the one or more formations of a first module comprise a rim of an end of a wall of the first module, the rim having a recess formed in a radially inner circumferential portion of the rim wherein the remaining portion of the rim defines a substantially circumferential skirt portion.

4. An assembly as claimed in claim 1 wherein the fluid inlet aperture and fluid outlet aperture of the at least one module are provided at substantially opposite locations of the wall of the chamber.

5. An assembly as claimed in claim 1 wherein the chamber is substantially cylindrical in shape.

6. An assembly as claimed in claim 1 further provided with a sample support arranged to support a sample in the form of a membrane, the support being arranged to allow each of a pair of opposed major faces of the membrane to be exposed to fluid contained within the chamber.

7. An assembly as claimed in claim 1 wherein the sample support comprises at least one support member arranged to contact a portion of the sample.

8. An assembly as claimed in claim 7 wherein the at least one support member comprises at least one post element.

9. An assembly as claimed in claim 8 wherein the at least one post element is provided with an upper surface arranged to contact a sample, the upper surface being one selected from amongst substantially flat, substantially curved and substantially domed.

10. An assembly as claimed in claim 1 wherein a cap module is provided comprising a module arranged to define a closed end of the chamber.

11. An assembly as claimed in claim 10 wherein the sample support is provided in the cap module.

12. An assembly as claimed in claim 1 wherein the modules are arranged to couple to one another at least in part by means of a friction fit.

13. An assembly as claimed in claim 1 wherein the complementary formations are formed from a material having a self-adhesive property.

14. An assembly as claimed in claim 1 wherein the complementary formations and a remainder of the modules are formed from substantially the same material.

15. An assembly as claimed in claim 1 wherein the complementary formations are formed from a silicone material.

16. An assembly as claimed in claim 1, wherein the first and second generally planar surface features are sufficiently resiliently deformable so as to form a liquid-tight seal without a separate seal element.

17. An assembly as claimed in claim 1, wherein the first module is formed as a single unitary member and the second module is formed as a single unitary member.

18. A bioreactor apparatus comprising:
a plurality of bioreactor chamber assemblies, each of the bioreactor chamber assemblies comprising:
a chamber comprising a plurality of modules arranged to be coupled together to form the chamber, the chamber being arranged wherein one or more barriers are provided within the chamber to define a plurality of fluid reservoirs, at least one module of the chamber having a fluid inlet aperture and a fluid outlet aperture arranged to establish fluid flow through a reservoir,
wherein respective modules are provided with one or more respective complementary formations arranged such that the modules are configured to be coupled to one another, the complementary formations comprising a resiliently deformable material and arranged to form a liquid-tight seal between the respective formations without a requirement for a separate seal element,
wherein the complementary comprise a first generally planar surface feature on a first module of the plurality of modules that interacts with a corresponding second generally planar surface feature on a second module of the plurality of modules such that the first and second generally planar surface features are sufficiently resiliently deformable so as to form a liquid-tight seal;

wherein a first reservoir of a first chamber assembly is coupled to a first reservoir of a second chamber assembly.

19. An Apparatus as claimed in claim 18 wherein the first reservoirs of the first and second chambers are coupled in series and configured such that fluid flows through the first reservoir of the first chamber and subsequently through the first reservoir of the second chamber.

20. A bioreactor chamber assembly comprising:

a bioreactor chamber comprising first and second portions arranged to be coupled to one another so as to provide a liquid-tight seal therebetween;

a pair of clamp members; and a pair of resilient loop elements, wherein the clamp members are arranged to sandwich the chamber between the clamp members and the loop elements are arranged to apply a force between the clamp members to urge the first and second portions together, wherein the loop elements are arranged to apply a force between the clamp members transversely to the seal between the first and second portions of the bioreactor chamber, wherein the first and second portions each comprise complementary formations such that a first generally planar surface feature is on the first portion that interacts with a corresponding second generally planar surface feature on the second portion and the first and second generally planar surface features are sufficiently resiliently deformable so as to form a liquid-tight seal.

* * * * *

UNITED STATES PATENT AND TRADEMARK OFFICE
CERTIFICATE OF CORRECTION

PATENT NO.      : 8,735,144 B2  
APPLICATION NO. : 13/057068  
DATED           : May 27, 2014  
INVENTOR(S)     : Ahluwalia et al.

Page 1 of 1

It is certified that error appears in the above-identified patent and that said Letters Patent is hereby corrected as shown below:

In the Claims:

Column 14, Claim 18, Line 66:

Please correct "the complementary comprise"
to read -- the complementary formations comprise --

Signed and Sealed this
Twenty-third Day of December, 2014

Michelle K. Lee
*Deputy Director of the United States Patent and Trademark Office*